United States Patent [19]

Takase et al.

[11] Patent Number: 4,868,303
[45] Date of Patent: Sep. 19, 1989

[54] BIS-DIOXOPIPERAZINE DERIVATIVES

[75] Inventors: Muneaki Takase; Jun-Chao Cai, both of Tokyo, Japan

[73] Assignee: Zenyaku Kogyo Kabushiki Kaisha, Tokyo, Japan

[21] Appl. No.: 124,932

[22] PCT Filed: Feb. 5, 1987

[86] PCT No.: PCT/JP87/00074

§ 371 Date: Sep. 25, 1987

§ 102(e) Date: Sep. 25, 1987

[87] PCT Pub. No.: WO87/04707

PCT Pub. Date: Aug. 31, 1987

[30] Foreign Application Priority Data

Feb. 7, 1986 [JP] Japan .................................. 61-25191

[51] Int. Cl.⁴ .................. C07D 403/06; A61K 31/495
[52] U.S. Cl. .................................................... 544/357
[58] Field of Search ......................................... 544/357

[56] References Cited

U.S. PATENT DOCUMENTS

| 4,404,381 | 9/1983 | Woo | 544/357 |
| 4,536,564 | 8/1985 | Woo | 544/357 |
| 4,650,799 | 3/1987 | Cai | 544/357 |
| 4,737,497 | 4/1988 | Ren | 544/385 |
| 4,764,614 | 8/1988 | Miller | 544/357 |

FOREIGN PATENT DOCUMENTS

| 230474 | 8/1987 | European Pat. Off. | 544/357 |
| 2511891 | 10/1976 | Fed. Rep. of Germany | 544/357 |
| 2012129 | 2/1972 | France | 544/357 |
| 60-97963 | 5/1985 | Japan | 544/357 |
| 60-152660 | 7/1986 | Japan | 544/357 |
| 978724 | 12/1964 | United Kingdom | 544/357 |
| 1001157 | 8/1965 | United Kingdom | 544/357 |
| 1234935 | 6/1971 | United Kingdom | 544/357 |

OTHER PUBLICATIONS

Cai, Chemical Abstract, 106:293e.

Primary Examiner—Donald G. Daus
Attorney, Agent, or Firm—Scrivener and Clarke

[57] ABSTRACT

Novel bis-dioxopiperazine derivatives or pharmaceutically acceptable salts thereof having broader antitumor spectra and represented by the following formula (I):

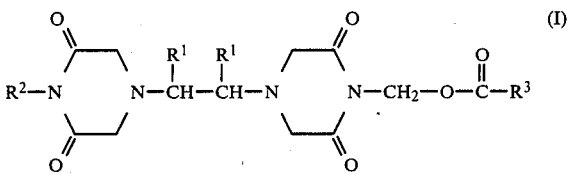

wherein
$R^1$ represents a lower alkyl group;
$R^2$ represents a hydrogen atom or a group of

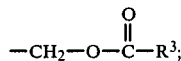

and
$R^3$ represents a lower alkyl group, a substituted or unsubstituted phenyl group, a substituted or unsubstituted furyl group, a substituted or unsubstituted styryl group or a group of $-(CH_2)_n-R^4$,

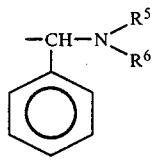

or $-OR^7$
in which
$R^4$ represents a carboxyl group, a substituted or unsubstituted phenyl group or a substituted or unsubstituted phenoxy group,
$R^5$ and $R^6$ respectively represent a hydrogen atom or a protective group for amino group,
$R^7$ represents a lower alkyl group or a substituted or unsubstituted benzyl group, and
n is an integer and 1 or 2.

20 Claims, No Drawings

BIS-DIOXOPIPERAZINE DERIVATIVES

TECHNICAL FIELD

The present invention relates to bis-dioxopiperazine derivatives having antitumor activity and pharmaceutically acceptable salts thereof.

BACKGROUND ART

Several kinds of bis-dioxopiperazine derivatives have been already reported. Among them, especially known as compounds having antitumor activity are 1,2-bis(4-morpholinomethyl-3,5-dioxopiperazin-1-yl)ethane (see Abstract, 8th International Congress of Pharmacology p 441, 1981), dl-1,2-bis(4-morpholinomethyl-3,5-dioxopiperazin-1-yl)propane (see Japanese Patent Provisional Publication No. 59-190976 and European Patent Publication No. 0125475A1) and 1,2-bis(4-isobutoxycarbonyloxymethyl-3,5-dioxopiperazin-1-yl)ethane (see Abstract, 14th International Congress of Chemotherapy p 324, 1985, Japanese Patent Provisional Publication No. 60-97963 and European Patent Publication No. 0140327A2).

Still, there has been a demand for a bis-dioxopiperazine derivative having more excellent antitumor activity than those known compounds.

DISCLOSURE OF THE INVENTION

Under such circumstances, we, the inventors further carried out studies on novel bis-dioxopiperazine derivatives. As a result, we found that the below-mentioned bis-dioxopiperazine derivatives of formula (I) exhibit remarkably excellent antitumor activity.

A compound of the present invention is represented by the formula (I):

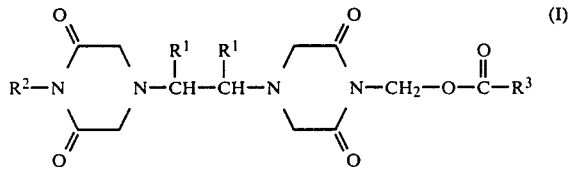

wherein
$R^1$ represents a lower alkyl group;
$R^2$ represents a hydrogen atom or a group of

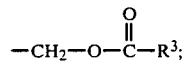

and
$R^3$ represents a lower alkyl group, a substituted or unsubstituted phenyl group, a substituted or unsubstituted furyl group, a substituted or unsubstituted styryl group or a group of $-(CH_2)_n-R^4$,

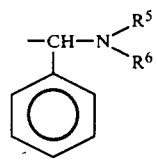

or $-OR^7$
in which $R^4$ represents a carboxyl group, a substituted or unsubstituted phenyl group or a substituted or unsubstituted phenoxy group,
$R^5$ and $R^6$ respectively represent a hydrogen atom or a protective group for amino group,
$R^7$ represents a lower alkyl group or a substituted or unsubstituted benzyl group, and
n is an integer and 1 and 2,
a substituent for the phenyl group, the phenoxy group and the benzyl group being selected from the group consisting of a halogen atom, a lower alkyl group, a lower alkoxy group, a nitro group, an amino group and a cyano group,
a substituent for the phenyl group, the furyl group and the styryl group being selected from the group consisting of a halogen atom, a lower alkyl group, a lower alkoxy group, a nitro group, an amino group and a cyano group.

Terms used for definition of letters in this formula are defined and exemplified in the following.

The term "lower" refers to from 1 to 6 carbon atoms unless otherwise indicated.

The "lower alkyl group" may be selected from the group having a normal or branched carbon chain such as methyl, ethyl, n-propyl, isopropyl, n-butyl, isobutyl, tert-butyl, n-pentyl and n-hexyl. Preferably, methyl is used for $R^1$.

The "protective group for amino group" may be acetyl, tert-butoxycarbonyl or benzyloxycarbonyl.

When the benzene ring such as the phenyl group, the styryl group, the benzyl group or the phenoxy group or the furyl group has a substituent, such substituent may be a halogen atom such as fluorine, chlorine or bromine, a lower alkyl group such as methyl or ethyl, a lower alkoxy group such as methoxy or ethoxy, a nitro group, an amino group or a cyano group. The benzene ring or the furyl group may have two substituents.

The compound of the present invention is for example as follows:

2,3-bis(4-acetoxymethyl-3,5-dioxopiperazin-1-yl)butane
2,3-bis(4-n-butyryloxymethyl-3,5-dioxopiperazin-1-yl)butane
2,3-bis(4-β-carboxypropionyloxmethyl-3,5-dioxopiperazin-1-yl)butane
2,3-bis(4-phenylacetoxymethyl-3,5-dioxopiperazin-1-yl)butane
2,3-bis[4-(2-chlorophenylacetoxymethyl)-3,5-dioxopiperazin-1-yl]butane
2,3-bis(4-phenoxyacetoxymethyl-3,5-dioxopiperazin-1-yl)butane
2,3-bis[4-(2,4-dichlorophenoxyacetoxymethyl)-3,5-dioxopiperazin-1-yl]butane
2,3-bis(4-cinnamoyloxymethyl-3,5-dioxopiperazin-1-yl)butane
2,3-bis[4-(3-chlorocinnamoyloxymethyl)-3,5-dioxopiperazin-1-yl]butane
2,3-bis[4-(2-N-acetylamino-2-phenylacetoxymethyl)-3,5-dioxopiperazin-1-yl]butane
2,3-bis[4-(2-N-tert-butoxycarbonylamino-2-phenylacetoxymethyl)-3,5-dioxopiperazin-1-yl]butane
2,3-bis[4-(2-amino-2-phenylacetoxymethyl)-3,5-dioxopiperazin-1-yl]butane trifluoroacetate
2,3-bis(4-benzoyloxymethyl-3,5-dioxopiperazin-1-yl)butane
2,3-bis[4-(2-methoxybenzoyloxymethyl)-3,5-dioxopiperazin-1-yl]butane 2,3-bis[4-(3-toluoyloxymethyl)-3,5-dioxopiperazin-1-yl]butane 2,3-bis(4-furoyloxymethyl-3,5-dioxopiperazin-1-yl)butane 2,3-bis(4-methoxycarbonyloxymethyl-3,5-dioxopiperazin-1-yl)butane 2,3-bis(4-isobutoxycarbonyloxymethyl-3,5-dioxopiperazin-1-yl)butane 2,3-bis(4-benzyloxycarbonyloxymethyl-3,5-dioxopiperazin-1-yl)butane 2,3-bis[4-(4-nitrobenzyloxycarbonylmethyl)-3,5-dioxopiperazin-1-yl]butane 2-(4-acetoxymethyl-3,5-dioxopiperazin-1-yl)-3-(3,5-dioxopiperazin-1-yl)butane 2-(4-β-carboxypropionyloxymethyl-3,5-dioxopiperazin-1-yl)-3-(3,5-dioxopiperazin-1-yl)butane 2-[4-(2-chlorophenylacetoxymethyl)-3,5-dioxopiperazin-1-yl]-3-(3,5-dioxopiperazin-1-yl)butane 2-[4-(2,4-dichlorophenoxyacetoxymethyl)-3,5-dioxopiperazin-1-yl]-3-(3,5-dioxopiperazin-1-yl)butane 2-[4-(3-chlorocinnamoyloxymethyl)-3,5-dioxopiperazin-1-yl]-3-(3,5-dioxopiperazin-1-yl)butane 2-[4-(2-N-tert-butoxycarbonylamino-2-phenylacetoxymethyl)-3,5-dioxopiperazin-1-yl]-3-(3,5-dioxopiperazin-1-yl)butane 2-[4-(2-amino-2-phenylacetoxymethyl)-3,5-dioxopiperazin-1-yl]-3-(3,5-dioxopiperazin-1-yl)butane trifluoroacetate 2-(4-benzoyloxymethyl-3,5-dioxopiperazin-1-yl)-3-(3,5-dioxopiperazin-1-yl)butane 2-[4-(3-toluoyloxymethyl)-3,5-dioxopiperazin-1-yl]-3-(3,5-dioxopierazin-1-yl)butane 2-(4-furoyloxymethyl-3,5-dioxopiperazin-1-yl)-3-(3,5-dioxopiperazin-1-yl)butane 2-(4-methoxycarbonyloxymethyl-3,5-dioxopiperazin-1-yl)-3-(3,5-dioxopiperazin-1-yl)butane 2-(4-isobutoxycarbonyloxymethyl-3,5-dioxopiperazin-1-yl)-3-(3,5-dioxopiperazin-1-yl)butane 2-(4-benzyloxycarbonyloxymethyl-3,5-dioxopiperazin-1-yl)-3-(3,5-dioxopiperazin-1-yl)butane 2-[4-(4-nitrobenzyloxycarbonyloxymethyl)-3,5-dioxopiperazin-1-yl]-3-(3,5-dioxopiperazin-1-yl)butane The compound (I) of the present invention has asymmetric carbon atoms in its molecules. It is to be understood that isomers due to such asymmetric carbon atom or combination of any of the isomers are included in the category of the compound (I). Especially, meso- or erythro-form is preferred.

The compound (I) of the present invention may be in the form of pharmaceutically acceptable salt such as hydrochloride, oxalate, p-toluenesulfonate, acetate or trifluoroacetate.

The compound (I) of the present invention may be prepared by reacting a compound represented by the formula (II):

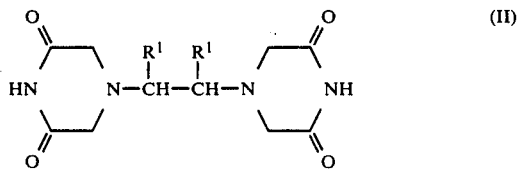

(II)

wherein $R^1$ is as defined above, with formaldehyde and then reacting the resultant compound with a compound represented by the formula (III) or a reactive derivative thereof:

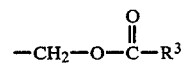

wherein $R^3$ is as defined above.

In the reaction of the compound of the formula (II) with formaldehyde, at least two equivalent molar amount of formaldehyde should be used to one molar amount of the compound of the formula (II), the reaction being effected in N,N-dimethylformamide (DMF) at 100° to 150° C.

Then, the resultant compound is reacted, without isolation, with the compound of the formula (III) or its reactive derivative. In this case, the following manner (A) or (B) may be employed:

(A) When the compound of the formula (III) is used, the reaction is effected in the presence of a condensing agent apart from a case where the compound of the present invention is the compound of the formula (III) in which $R^3$ represents a group of $-OR^7$ (in which $R^7$ is as defined above).

The condensing agent may be, for example, 1-methyl-2-chloropyridinium iodide, 2-chloro-3-ethylbenzoxazolium tetrafluoroborate, dicyclohexylcarbodiimide or N,N'-carbonyldiimidazole. Preferably, methyl iodide is used as reaction accelerator in the case of N,N'-carbonyldiimidazole being a condensing agent used; and dimethylaminopyridine, in the case of the other condensing agents.

The reaction temperature may range from 0° to 50° C., and the reaction time may range from 4 to 24 hours which depends on reaction temperature.

(B) When a reactive derivative of the compound (III) is used, such derivative in preferably acid halide, acid anhydride or haloformate.

The reaction temperature may range from −20° C. to room temperature and the reaction time may range from 1 to 8 hours which depends on reaction temperature.

In the manner (A) or (B), 0.8 to 5 molar amount of the compound of the formula (III) or reactive derivative thereof is used to one molar amount of the compound of the formula (II). As for the reaction solvent, an aprotic polar solvent such as DMF, pyridine, dichloromethane, chloroform, acetonitrile or their mixture may be used.

In the above-mentioned preparation process, the compounds of the formula (I) in which $R^2$ is hydrogen atom and the group of $$-CH_2-O-\overset{O}{\underset{\|}{C}}-R^3$$

are concurrently generated whose generation ratio depends on the used amount of the compound of the formula (III) or reactive derivative thereof relative to that of the compound of the formula (II), and are separated and purified according to ordinary method using silica gel column chromatography or the like.

Upon preparation of the compound of the formula (I) according to the present invention, functional group of the compound of the formula (III) is protected according to ordinary method as needs demands.

Pharmaceutically acceptable salts of the compound of the formula (I) according to the present invention, e.g., hydrochloride, oxalate, p-toluenesulfonate, acetate and trifluoroacetate thereof may be prepared according to ordinary method.

The compound of the formula (II) which is the starting material in the above-mentioned process of the present invention is a known compound and can be prepared according to a process described in British Patent Specification No. 1234935.

The antitumor activity of the compound of the formula (I) according to the present invention and prepared by the above-mentioned process, was verified by the below-mentioned tests. The test samples in these tests were as follows:

Sample 1: meso-2,3-bis(4-acetoxymethyl-3,5-dioxopiperazin-1-yl)butane

Sample 2: meso-2,3-bis[4-(2-chlorophenylacetoxymethyl)-3,5-dioxopiperazin-1-yl]butane Sample 3: meso-2,3-bis[4-(2,4-dichlorophenoxyacetoxymethyl)-3,5-dioxopiperazin-1-yl]butane Sample 4: meso-2,3-bis[4-(3-chlorocinnamoyloxymethyl)-3,5-dioxopiperazin-1-yl]butane Sample 5: meso-2,3-bis[4-[(R)-2-N-tert-butoxycarbonylamino-2-phenylacetoxymethyl]-3,5-dioxopiperazin-1-yl]butane Sample 6: meso-2,3-bis[4-[(R)-2-amino-2-phenylacetoxymethyl]-3,5-dioxopiperazin-1-yl]butane trifluoroacetate Sample 7: meso-2,3-bis(4-isobutoxycarbonyloxymethyl-3,5-dioxopiperazin-1-yl)butane Sample 8: meso-2,3-bis[4-(4-nitrobenzyloxycarbonyloxymethyl)-3,5-dioxopiperazin-1-yl]butane Sample 9: erythro-2-(4-acetoxymethyl-3,5-dioxopiperazin-1-yl)-3-(3,5-dioxopiperazin-1-yl)butane Sample 10: erythro-2-[4-(2-chlorophenylacetoxymethyl)-3,5-dioxopiperazin-1-yl]-3-(3,5-dioxopiperazin-1-yl)butane Sample 11: erythro-2-[4-(2,4-dichlorophenoxyacetoxymethyl)-3,5-dioxopiperazin-1-yl]-3-(3,5-dioxopiperazin-1-yl)butane Sample 12: erythro-2-[4-(3-chlorocinnamoyloxymethyl)-3,5-dioxopiperazin-1-yl]-3-(3,5-dioxopiperazin-1-yl)butane Sample 13: erythro-2-(4-benzoyloxymethyl-3,5-dioxopiperazin-1-yl)-3-(3,5-dioxopiperazin-1-yl)butane Sample 14: erythro-2-[4-(3-toluoyloxmethyl)-3,5-dioxopiperazin-1-yl]-3-(3,5-dioxopiperazine-1-yl)butane Sample 15: erythro-2-[4-(4-nitrobenzyloxycarbonyloxymethyl)-3,5-dioxopiperazin-1-yl]-3-(3,5-dioxopiperazin-1-yl)butane Sample 16: meso-2,3-bis(4-benzoyloxymethyl-3,5-dioxopiperazin-1-yl)butane Sample 17: meso-2,3-bis(4-benzyloxycarbonyloxymethyl-3,5-dioxopiperazin-1-yl)butane Sample 18: erythro-2-[4-(2-furoyloxymethyl)-3,5-dioxopiperazin-1-yl]-3-(3,5-dioxopiperazin-1-yl)butane Sample 19: erythro-2-(4-benzyloxycarbonyloxymethyl-3,5-dioxopiperazin-1-yl)-3-(3,5-dioxopiperazin-1-yl)butane

COMPARATIVE COMPOUNDS

Sample A: 1,2-bis(4-isobutoxycarbonyloxymethyl-3,5-dioxopiperazin-1-yl)ethane

Sample B: meso-2,3-bis(3,5-dioxopiperazin-1-yl)butane (Typical starting material for the compound of the present invention)

(I) Growth Inhibition of Tumor Cells of P388 Lymphocytic Leukemia in Vitro:

Tumor cells were collected aseptically with capillary tube from ascites in $CDF_1$ female mice transplanted intraperitoneally with $1 \times 10^6$ cells of P388 lymphocytic leukemia 5 days before. Cell suspension was prepared at $5 \times 10^4$ cells/0.5 ml in a RPMI1640 medium supplemented with 10% fetal calf serum, kanamycin (0.1 mg/ml) and 2-hydroxyethyldisulfide (0.01 mM). Each test sample was dissolved or suspended in the medium at a concentration of $1 \times 10^{-1} - 1 \times 10^{-5}$ mM.

A test tube with Molton stopper loosely involving 0.5 ml each of the cell suspension and the sample suspension was kept for 48 hours at 37° C. in an incubator supplied with air containing 5% carbon dioxide. Then, after addition of 4 ml of 0.25% trypsin solution, the tube was shaken for 5 minutes at 37° C. The cells harvested therefrom was counted by using of a Coulter Counter and the inhibition of cell growth was calculated by the following formula:

Growth Inhibition $(\%) = (1 - T/C) \times 100$

T: number of cells in the culture containing test sample
C: number of cells in the culture of control 50% Inhibitory concentration of cell growth ($IC_{50}$) was calculated based on the inhibition in various concentrations of test compound and is shown in Table 1.

TABLE 1

| Sample | $IC_{50}$(mM) | Sample | $IC_{50}$ (mM) |
| --- | --- | --- | --- |
| 1 | $3.0 \times 10^{-4}$ | 11 | $7.7 \times 10^{-5}$ |
| 2 | $8.6 \times 10^{-6}$ | 12 | $1.1 \times 10^{-5}$ |
| 3 | $7.1 \times 10^{-5}$ | 13 | $3.8 \times 10^{-5}$ |
| 4 | $2.4 \times 10^{-4}$ | 14 | $1.3 \times 10^{-5}$ |
| 5 | $3.2 \times 10^{-5}$ | 15 | $2.4 \times 10^{-4}$ |
| 6 | $5.2 \times 10^{-5}$ | 16 | $2.5 \times 10^{-4}$ |
| 7 | $8.4 \times 10^{-5}$ | 17 | $5.6 \times 10^{-5}$ |
| 8 | $1.5 \times 10^{-4}$ | 18 | $4.2 \times 10^{-5}$ |
| 9 | $7.4 \times 10^{-5}$ | 19 | $1.1 \times 10^{-5}$ |
| 10 | $7.1 \times 10^{-6}$ | A | $1.6 \times 10^{-2}$ |

It was found that the compounds of the present invention exhibit remarkably strong growth inhibition activity against P388 lymphocytic leukemia cells and are effective in concentration about one-hundredth or more as little as that of the structurally analogous comparative compound A.

The fact that the compound of the present invention exhibits specifically stronger activity than the comparative compound A and is effective in by far lower dose than the latter will enable the compound of the present invention to be locally applied in higher concentration to patient in the form of microcapsule, injection or the like. Such local application will serve for reduction of patient's load upon administration and contribute to prevention of systemic side effects on patient.

(II) Inhibitory effect on Colony Formation of V79 Cells in Vitro:

V79 cells established from Chinese hamster lung fibroblastoma were cultured routinely on plastic dishes ($\phi$ 60 mm) in RPMI 1640 medium supplemented with 10% fetal calf serum and kanamycin (0.1 mg/ml). Each confluent culture was then trypsinized by the addition of 1 ml of trypsin-EDTA solution (supplied by the firm GIBCO) for 5 minutes at 37° C. in an incubator supplied with humidified air containing 5% $CO_2$.

Homogeneous suspension of V79 cells thus obtained was diluted to 100, 200 and 400 viable cells/ml with the medium, and 1 ml each of them was transferred to other plastic dishes ($\phi$ 60 mm) containing 1.85 ml of the medium, and diluted to 100, 200 and 400 viable cells/dish.

Each test sample was dissolved in DMSO at the concentration of 20 mM and diluted with the medium to the final concentration of $2\times10^{-3}$–$2\times10^{-10}$ mM.

Each test dish was kept for 24 hours at 37° C. in an incubator supplied with humidified air containing 5% $CO_2$, and was further cultured for 96 hours after 150 μl of the sample solution was added thereto.

The cells were gently washed once with Mg- and Ca-free phosphate-buffered saline [PBS(—)] and fixed with 1 ml of 3.5% HCHO-PBS(—) solution for 2 hours, then stained with a crystal violet ethanol solution.

The 90% inhibitory concentration ($IC_{90}$) was calculated by comparing the number of visible colonies on the sample dish with that on the control dish.

The results were shown in Table 2.

TABLE 2

| Sample | $IC_{90}$(mM) | Sample | $IC_{90}$(mM) |
|---|---|---|---|
| 1 | $8.9 \times 10^{-8}$ | 16 | $9.8 \times 10^{-8}$ |
| 7 | $4.5 \times 10^{-9}$ | 18 | $1.0 \times 10^{-7}$ |
| 10 | $7.3 \times 10^{-8}$ | 19 | $9.0 \times 10^{-8}$ |
| 11 | $8.2 \times 10^{-8}$ | A | $1.1 \times 10^{-4}$ |
| 12 | $9.8 \times 10^{-8}$ | B | $5.3 \times 10^{-6}$ |
| 14 | $5.1 \times 10^{-8}$ | | |

(III) Increase in Life Span on P388 Lymphocytic Leukemia Tumor-transplanted Mouse:

The treated group to which the test sample was administered consisted of seven mice, while the control group consisted of ten mice. Six weeks old male mice ($CDF_1$, 25±2 g of body weight) were employed as host animals.

Tumor cells ($1.0\times10^6$) of P388 lymphocytic leukemia were transplanted intraperitoneally into each mouse. The treatment was effected one day after the transplantation and on 5th day by administering prescribed dose of each test sample intraperitoneally to the mice.

Antitumor activity of the test sample was evaluated by the rate of increase in life span (ILS) which was calculated with the following formula.

$$\text{ILS }(\%)=(T'/C'-1)\times 100$$

T': median survival time of treated mice
C': median survival time of control mice The results obtained from the above-mentioned test are shown in Table 3.

TABLE 3

| Sample | Daily Dose (mg/kg) | ILS (%) | Sample | Daily Dose (mg/kg) | ILS (%) |
|---|---|---|---|---|---|
| 1 | 1.5 | 152 | 15 | 2.6 | 177 |
| 2 | 3.4 | 107 | 16 | 3.0 | 150 |
| 7 | 3.0 | 104 | 17 | 3.2 | 179 |
| 10 | 2.5 | 162 | 18 | 2.2 | 185 |
| 11 | 2.7 | 132 | 19 | 2.4 | 132 |
| 12 | 2.5 | 90 | A | 250* | 106 |
| 13 | 2.2 | 118 | | 3.0 | 5 |
| 14 | 2.3 | 199 | | | |

*Adequate dose

The fact that the compound of the present invention exhibits remarkably excellent ILS on P388 lymphocytic leukemia tumor-transplanted mice will reveal said compound to have strong antitumor activity and indicate the utility of the same as antitumor agent for animal and human.

It was found that the compounds of the present invention exhibit a broader antitumor spectrum in antitumor activity tests using L1210 lymphoid leukemia, B-16 melanoma, Lewis lung carcinoma, MM-46 mammary carcinoma, MH-134 hepatoma and Ehrlich carcinoma.

The acute toxicity of the compounds of the present invention was examined by the following test.

The test group to which the compound of the present invention was administered consisted of five mice. Six weeks old male mice (ddY, 30±2 g of body weight) were employed as test animals.

These animals were intraperitoneally given the test compound which was suspended in the saline solution containing hydroxypropyl cellulose (HPC) by 1% and were observed for 14 days successively, and $LD_{50}$ value of acute toxicity was determined. As a result, $LD_{50}$ for erythro-2-[4-(3-toluoyloxymethyl)-3,5-dioxopiperazin-1-yl]-3-(3,5-dioxopiperazin-1-yl)butane was 6.7–10.0 mg/kg.

The following descriptions are given for the administration routes, pharmaceutical forms and doses when bis-dioxopiperazine derivatives of the present invention are applied to human.

The compounds of the present invention may be administered orally in forms such as tablets, coated tablets, powders, granules, capsules, microcapsules, syrups and so on. They may be also administered parenterally in forms such as injections which may include dissolvable freeze-drying form, suppositories and so on.

In the preparation of these forms, pharmaceutically acceptable diluent bases, binders, disintegrators, lubricants, suspensions, emulsifiers, antiseptics, stabilizers and dispersing agents, for example, lactose, sucrose, starch, dextrin, crystalline cellulose, kaolin, calcium carbonate, talc, magnesium stearate, distilled water and physiological saline solution may be used.

Although the daily doses of these compounds may be varied according to the conditions, ages and weights of the subjects to be treated, the daily doses to adult humans may normally fall within the range of 1 to 600 mg, preferably 5 to 100 mg, and may be divided into two or three portions.

BEST MODE FOR CARRYING OUT THE INVENTION

The invention illustrated by the following examples, but it should be noted that the present invention is not limited to the examples.

EXAMPLE 1

Meso-2,3-bis(4-acetoxymethyl-3,5-dioxopiperazin-1-yl)butane and
erythro-2-(4-acetoxymethyl-3,5-dioxopiperazin-1-yl)-3-(3,5-dioxopiperazin-1-yl)butane A mixture of meso-2,3-bis(3,5-dioxopiperazin-1-yl)butane (200 mg, 0.7 mmol) and DMF (4 ml) was heated at 110° C. for 10 minutes. To the mixture, 37% aqueous formaldehyde solution (0.2 ml) was added, and then the mixture was stirred at 140° C. for 1.5 hour. The solvent was removed from the reaction mixture under reduced pressure and the residue was added with DMF (4 ml) and pyridine (1 ml) and cooled to 0° C. The cooled mixture was added with acetyl chloride (0.1 ml, 1.5 mmol) and stirred at 0° C. for 1 hour and further at room temperature for 2 hours. Then, the solvent was removed from the reaction mixture under reduced pressure and the residue was extracted with chloroform. The chloroform solution was washed with diluted hydrochloric acid, aqueous solution of saturated sodium bicarbonate and water, and was dried over anhydrous magnesium sulfate. The solvent was removed from the chloroform solution under reduced pressure and the obtained residue was purified by column chromatography on silica gel, using ethyl acetate-n-hexane (=1:1) as an eluant to give the titled compound.

Meso-2,3-bis(4-acetoxymethyl-3,5-dioxopiperazin-1-yl)butane
  Yield: 23 mg, 8%.
  Melting point: 222°–225° C.
  IR spectrum (KBr) cm$^{-1}$: 1700, 1760 (C=O)
  NMR spectrum (CDCl$_3$)δ ppm: 1.06 (6H, d, J=6 Hz), 2.06 (6H, s), 2.64 (2H, m), 3.43 (4H, d, J=17 Hz), 3.54 (4H, d, J=17 Hz), 5.77 (4H, s).

Erythro-2-(4-acetoxymethyl-3,5-dioxopiperazin-1-yl)-3-(3,5-dioxopiperazin-1-yl)butane
  Yield: 43 mg, 17%.
  Melting point: 182°–186° C.
  IR spectrum (KBr) cm$^{-1}$: 1710, 1740 (C=O).
  NMR spectrum (CDCl$_3$)δ ppm: 1.07 (6H, d, J=5 Hz), 2.06 (3H, s), 2.62 (2H, m), 3.2–3.6 (8H, m), 5.77 (2H, s), 7.90 (1H, broad s).

In accordance with the procedure of Example 1, the following compounds were obtained from the corresponding starting materials.

Meso-2,3-bis(4-benzoyloxymethyl-3,5-dioxopiperazin-1-yl)butane
  Melting point: 144°–148° C.
  IR spectrum (KBr) cm$^{-1}$: 1700, 1720 (C=O).
  NMR spectrum (CDCl$_3$)δ ppm: 1.10 (6H, d, J=4 Hz), 2.70 (2H, m), 3.52 (4H, d, J=16 Hz), 3.61 (4H, d, J=16 Hz), 6.03 (4H, s), 7.3–8.1 (10H, m).

Meso-2,3-bis[4-(3-toluoyloxymethyl)-3,5-dioxopiperazin-1-yl]butane
  Melting point: 167°–172° C.
  IR spectrum (KBr) cm$^{-1}$: 1700, 1715 (C=O).
  NMR spectrum (CDCl$_3$)δ ppm: 1.08 (6H, d, J=6 Hz), 2.38 (6H, s), 2.65 (2H, m), 3.47 (4H, d, J=18 Hz), 3.58 (4H, d, J=18 Hz), 6.02 (4H, s). 7.2–7.9 (8, m), Meso-2,3-bis[4-(2-furoyloxymethyl)-3,5-dioxopiperazin-1-yl]butane
  Melting point: 256°–262° C.
  IR spectrum (KBr) cm$^{-1}$: 1695, 1715, 1740 (C=O).
  NMR spectrum (DMSO-d$_6$)δ ppm: 0.93 (6H, d, J=3 Hz), 2.55 (2H, m), 3.51 (4H, d, J=18 Hz), 3.60 (4H, d, J=18 Hz), 5.84 (4H, s), 6.70 (2H, m), 7.30 (2H, m), 7.98 (2H, m).

Erythro-2-(4-benzoyloxymethyl-3,5-dioxopiperazin-1-yl)-3-(3,5-dioxopiperazin-1-yl)butane
  Melting point: 182°–185° C.
  IR spectrum (KBr) cm$^{-1}$: 1700, 1715 (C=O).
  NMR spectrum (CDCl$_3$)δ ppm: 1.07 (6H, d, J=5 Hz), 2.65 (2H, m), 3.3–3.7 (8H, m), 6.03 (2H, s), 7.3–8.1 (6H, m).

Erythro-2-[4-(3-toluoyloxymethyl)-3,5-dioxopiperazin-1-yl]-3-(3,5-dioxopiperazin-1-yl)butane
  Melting point: 188°–192° C.
  IR spectrum (KBr) cm$^{-1}$: 1700, 1710 (C=O).
  NMR spectrum (CDCl$_3$)δ ppm: 1.07 (6H, d, J=5 Hz), 2.38 (3H, s), 2.65 (2H, m), 3.2–3.6 (8H, m), 6.02 (2H, s), 7.2–7.8 (4H, m), 8.01 (1H, broad s).

Erythro-2-[4-(2-furoyloxymethyl)-3,5-dioxopiperazin-1-yl]-3-(3,5-dioxopiperazin-1-yl)butane
  Melting point: 214°–217° C.
  IR spectrum (KBr) cm$^{-1}$: 1710, 1730, 1750 (C=O).
  NMR spectrum (CDCl$_3$)δ ppm: 1.07 (6H, d, J=5 Hz), 2.65 (2H, m), 3.3–3.7 (8H, m), 6.00 (2H, s), 6.50 (1H, m), 7.19 (1H, m), 7.58 (1H, m), 7.88 (1H, broad s).

EXAMPLE 2

Meso-2,3-bis(4-methoxycarbonyloxymethyl-3,5-dioxopiperazin-1-yl)butane and
erythro-2-(4-methoxycarbonyloxymethyl-3,5-dioxopiperazin-1-yl)-3-(3,5-dioxopiperazin-1-yl)butane A mixture of meso-2,3-bis(3,5-dioxopiperazin-1-yl)butane (150 mg, 0.5 mmol) and DMF (4 ml) was heated at 110° C. for 10 minutes. To the mixture, 37% aqueous formaldehyde solution (0.2 ml) was added and then the mixture was stirred at 140° C. for 1.5 hours. The solvent was removed from the reaction mixture under reduced pressure and the residue was added with DMF (5 ml) and pyridine (1 ml) and cooled to 0° C. The cooled mixture was added with methyl chloroformate (0.2 ml, 2.6 mmol) and stirred at 0° C. for 1 hour and further at room temperature for 16 hours. Then, the reaction mixture was treated in the same manner as Example 1 to give the titled compound.

Meso-2,3-bis(4-methoxycarbonyloxymethyl-3,5-dioxopiperazin-1-yl)butane
  Yield: 34 mg, 14%.
  Melting point: 208°–210° C.
  IR spectrum (KBr) cm$^{-1}$: 1700, 1750 (C=O).
  NMR spectrum (DMSO-d$_6$)δ ppm: 0.90 (6H, d, J=4 Hz), 2.81 (2H, m), 3.45 (4H, d, J=17 Hz), 3.57 (4H, d, J=17 Hz), 3.72 (6H, s), 5.66 (4H, s).

Erythro-2-(4-methoxycarbonyloxymethyl-3,5-dioxopiperazin-1-yl)-3-(3,5-dioxopiperazin-1-yl)butane
  Yield: 51 mg, 26%.
  Melting point: 213°–215° C.
  IR spectrum (KBr) cm$^{-1}$: 1705, 1755 (C=O).
  NMR spectrum (DMSO-d$_6$)δ ppm: 0.90 (6H, d, J=4 Hz), 2.80 (2H, m), 3.2–3.6(8H, m), 3.71 (3H, s), 5.66 (2H, s), 11.04 (1H, broad s).

In accordance with the procedure of Example 2, the following compounds were obtained from the corresponding starting materials.

Meso-2,3-bis(4-isobutoxycarbonyloxymethyl-3,5-dioxopiperazin-1-yl)butane
  Melting point: 137°–141° C.
  IR spectrum (KBr) cm$^{-1}$: 1710, 1755 (C=O).
  NMR spectrum (CDCl$_3$)δ ppm: 0.94 (12H, d, J=7 Hz), 1.05 (6H, d, J=6 Hz), 1.97 (2H, m), 2.61 (2H, m), 3.41 (4H, d, J=16 Hz), 3.52 (4H, d, J=16 Hz), 3.94 (4H, d, J=7 Hz), 5.81 (4H, s).

Meso-2,3-bis(4-benzyloxycarbonyloxymethyl-3,5-dioxopiperazin-1-yl)butane
  Melting point: 143°–145° C.
  IR spectrum (KBr) cm$^{-1}$: 1700, 1755 (C=O).
  NMR spectrum (DMSO-d$_6$)δ ppm: 0.88 (6H, d, J=3 Hz), 2.79 (2H, m), 3.45 (4H, d, J=14 Hz), 3.55 (4H, d, J=14 Hz), 5.16 (4H, s), 5.68 (4H, s), 7.37 (10H, s).

Meso-2,3-bis[4-(4-nitrobenzyloxycarbonyloxymethyl)-3,5-dioxopiperazin-1-yl]butane
  Melting point: 157°–162° C.
  IR spectrum (KBr) cm$^{-1}$: 1700, 1760 (C=O).
  NMR spectrum (CDCl$_3$)δ ppm: 1.04 (6H, d, J=6 Hz), 2.60 (2H, m), 3.41 (4H, d, J=17 Hz), 3.52 (4H, d, J=17 Hz), 5.27 (4H, s), 5.85 (4H, s), 7.53 (4H, d, J=9 Hz), 8.23 (4H, d, J=9 Hz).

Erythro-2-(4-isobutoxycarbonyloxymethyl-3,5-dioxopiperazin-1-yl)-3-(3,5-dioxopiperazin-1-yl)butane
  Melting point: 185°–190° C.
  IR spectrum (KBr) cm$^{-1}$: 1705, 1740 (C=O).
  NMR spectrum (CDCl$_3$)δ ppm: 0.94 (6H, d, J=7 Hz), 1.05 (6H, d, J=6 Hz), 1.97 (1H, m), 2.64 (2H, m), 3.2–3.6 (8H, m), 3.94 (4H, d, J=7 Hz), 5.81 (2H, s), 8.33 (1H, broad s).

Erythro-2-(4-benzyloxycarbonyloxymethyl-3,5-dioxopiperazin-1-yl)-3-(3,5-dioxopiperazin-1-yl)butane
  Melting point: 164°–168° C.
  IR spectrum (KBr) cm$^{-1}$: 1700, 1740 (C=O).
  NMR spectrum (DMSO-d$_6$) δ ppm: 0.89 (6H, d, J=3 Hz), 2.76 (2H, m), 3.1–3.5 (8H, m), 5.16 (2H, s), 5.68 (2H, s), 7.38 (5H, s), 11.02 (1H, broad s).

Erythro-2-[4-(4-nitrobenzyloxycarbonyloxymethyl)-3,5-dioxopiperazin-1-yl]-3-(3,5-dioxopiperazin-1-yl)butane
  Melting point: 168°–172° C.
  IR spectrum (KBr) cm$^{-1}$: 1700, 1745 (C=O).
  NMR spectrum (CDCl$_3$) δ ppm: 1.05 (6H, d, J=6 Hz), 2.61 (2H, m), 3.2–3.6 (8H, m), 5.27 (2H, s), 5.85 (2H, s), 7.54 (2H, d, J=9 Hz), 7.88 (1H, broad s), 8.23 (2H, d, J=9 Hz).

EXAMPLE 3

Meso-2,3-bis[4-(2-chlorophenylacetoxymethyl)-3,5-dioxopiperazin-1-yl]butane and erythro-2-[4-(2-chlorophenylacetoxymethyl)-3,5-dioxopiperazin-1-yl]-3-(3,5-dioxopiperazin-1-yl)butane A mixture of meso-2,3-bis(3,5-dioxopiperazin-1-yl)butane (150 mg, 0.5 mmol) and DMF (4 ml) was heated at 110° C. for 10 minutes. To the mixture, 37% aqueous formaldehyde solution (0.2 ml) was added, and then the mixture was stirred at 140° C. for 1.5 hours. The solvent was removed from the reaction mixture under reduced pressure and the residue was dissolved in dichloromethane (20 ml). A solution of 2-chlorophenyl acetic acid (340 mg, 2 mmol), methyl iodide (0.5 ml, 8 mmol) and N,N'-carbonyldiimidazole (320 mg, 2 mmol) in dichloromethane (20 ml) was stirred at room temperature for 1.5 hours, added dropwise with the above-mentioned solution of the residue in dichloromethane and then stirred at room temperature for 16 hours. Then, the solvent was removed from the reaction mixture under reduced pressure and the residue was extracted with chloroform. The chloroform solution was washed with aqueous solution of saturated sodium bicarbonate and water, and was dried over anhydrous magnesium sulfate. The solvent was removed from the chloroform solution under reduced pressure and the obtained residue was purified by column chromatography on silica gel, using ethyl acetate-n-hexane (=1:1) as an elutant to give the titled compound.

Meso-2,3-bis[4-(2-chlorophenylacetoxymethyl)-3,5-dioxopiperazin-1-yl]butane
  Yield: 60 mg, 17%.
  Melting point: 178°–182° C.
  IR spectrum (KBr) cm$^{-1}$: 1705, 1755 (C=O).
  NMR spectrum (CDCl$_3$) δ ppm: 1.03 (6H, d, J=5 Hz), 2.62 (2H, m), 3.41 (4H, d, J=17 Hz), 3.53 (4H, d, J=17 Hz), 3.77 (4H, s), 5.83 (4H, s), 7.1–7.5 (8H, m).

Erythro-2-[4-(2-chlorophenylacetoxymethyl)-3,5-dioxopiperazin-1-yl]-3-(3,5-dioxopiperazin-1-yl)butane
  Yield: 45 mg, 18%.
  Melting point: 176°–179° C.
  IR spectrum (KBr) cm$^{-1}$: 1700, 1735 (C=O).
  NMR spectrum (CDCl$_3$) δ ppm: 1.04 (6H, d, J=6 Hz), 2.60 (2H, m), 3.2–3.6 (8H, m), 3.77 (2H, s), 5.83 (2H, s), 7.1–7.5 (4H, m), 7.92 (1H, broad s).

In accordance with the procedure of Example 3, the following compounds were obtained from the corresponding starting materials.

Meso-2,3-bis[4-(2,4-dichlorophenoxyacetoxymethyl)-3,5-dioxopiperazin-1-yl]butane
  Melting point: 185°–188° C.
  IR spectrum (KBr) cm$^{-1}$: 1700, 1740, 1770 (C=O).
  NMR spectrum (CDCl$_3$) δ ppm: 1.04 (6H, d, J=6 Hz), 2.66 (2H, m), 3.43 (4H, d, J=17 Hz), 3.54 (4H, d, J=17 Hz), 4.69 (4H, s), 5.88 (4H, s), 6.78 (2H, d, J=9 Hz), 7.17 (2H, dd, J=9 Hz.2 Hz), 7.37 (2H, d, J=2 Hz).

Meso-2,3-bis[4-(3-chlorocinnamoyloxymethyl)-3,5-dioxopiperazin-1-yl]butane
  Melting point: 168°–171° C.
  IR spectrum (KBr) cm$^{-1}$: 1705, 1740 (C=O).
  NMR spectrum (DMSO-d$_6$) δ ppm: 0.94 (6H, d, J=4 Hz), 2.84 (2H, m), 3.48 (4H, d, J=18 Hz), 3.60 (4H, d, J=18 Hz), 5.77 (4H, s), 6.74 (2H, d, J=16 Hz), 7.4–7.9 (10H, m).

Meso-2,3-bis[4-[(R)-2-N-tert-butoxycarbonylamino-2-phenylacetoxymethyl]-3,5-dioxopiperazin-1-yl]butane
  Melting point: 97°–102° C.
  IR spectrum (KBr) cm$^{-1}$: 1700, 1750 (C=O).
  NMR spectrum (CDCl$_3$) δ ppm: 0.97 (6H, d, J=6 Hz), 1.42 (18H, s), 2.54 (2H, m), 3.33 (4H, d, J=17 Hz), 3.43 (4H, d, J=17 Hz), 5.31 (2H, d, J=5 Hz), 5.48 (2H, d, J=5 Hz), 5.83 (4H, s), 7.32 (10H, s).

Meso-2,3-bis(4-β-carboxypropionyloxymethyl-3,5-dioxopiperazin-1-yl)butane
  Melting point: 169°–173° C.
  IR spectrum (KBr) cm$^{-1}$: 1700, 1740 (C=O).
  NMR spectrum (DMSO-d$_6$) δ ppm: 0.90 (6H, d, J=4 Hz), 2.4–2.6 (8H, m), 3.46 (4H, d, J=17 Hz), 3.57 (4H, d, J=17 Hz), 5.62 (4H, s), 12.25 (2H, broad s).

Erythro-2-[4-(2,4-dichlorophenoxyacetoxymethyl)-3,5-dioxopiperazin-1-yl]-3-(3,5-dioxopiperazin-1-yl)butane
  Melting point: 181°–184° C.
  IR spectrum (KBr) cm$^{-1}$: 1700, 1735, 1750 (C=O).
  NMR spectrum (CDCl$_3$) δ ppm: 1.06 (6H, d, J=5 Hz), 2.65 (2H, m), 3.2–3.6 (8H, m), 4.69 (2H, s), 5.88 (2H, s), 6.78 (1H, d, J=9 Hz), 7.17 (1H, dd, J=9 Hz.2 Hz), 7.38 (1H, d, J=2 Hz), 7.85 (1H, broad s).

Erythro-2-[4-(3-chlorocinnamoyloxymethyl)-3,5-dioxopiperazin-1-yl]-3-(3,5-dioxopiperazin-1-yl)butane
  Melting point: 164°–168° C.
  IR spectrum (KBr) cm$^{-1}$: 1700, 1720, 1745 (C=O).
  NMR spectrum (DMSO-d$_6$) δ ppm: 0.91 (6H, d, J=4 Hz), 2.80 (2H, m), 3.2–3.7 (8H, m), 5.77 (2H, s), 6.74 (1H, d, J=16 Hz), 7.4–7.9 (5H, m), 11.07 (1H, broad s).

Erythro-2-[4-[(R)-N-tert-butoxycarbonylamino-2-phenylacetoxymethyl]-3,5-dioxopiperazin-1-yl]-3-(3,5-dioxopiperazin-1-yl)butane
  Melting point: 109°–114° C.
  IR spectrum (KBr) cm$^{-1}$: 1700, 1750 (C=O).
  NMR spectrum (CDCl$_3$) δ ppm: 0.98 (6H, d, J=6 Hz), 1.42 (9H, s), 2.57 (2H, m), 3.2–3.5 (8H, m), 5.32 (1H, d, J=5 Hz), 5.54 (1H, d, J=5 Hz), 5.83 (2H, s), 7.32 (10H, s), 8.46 (1H, broad s).

Erythro-2-(4-β-carboxypropionyloxymethyl-3,5-dioxopiperazin-1-yl)-3-(3,5-dioxopiperazin-1-yl)butane
  Melting point: 144°–147° C.
  IR spectrum (KBr) cm$^{-1}$: 1700, 1730 (C=O).
  NMR spectrum (DMSO-d$_6$) δ ppm: 0.89 (6H, d, J=4 Hz), 2.4–2.6 (4H, m), 2.77 (2H, m), 3.1–3.6 (8H, m), 5.62 (2H, s), 11.06 (1H, broad s), 12.25 (1H, broad s).

EXAMPLE 4

Meso-2,3-bis[4-[(R)-2-amino-2-phenylacetoxymethyl]-3,5-dioxopiperazin-1-yl]butane trifluoroacetate A solution of meso-2,3-bis[4-[(R)-2-N-tert-butoxycarbonylamino-2-phenylacetoxymethyl]-3,5-dioxopiperazin-1-yl]butane (70 mg, 1 mmol) in trifluoroacetic acid (1 ml, 13 mmol) was stirred at 0° C. for 4 hours. The solvent was removed from the reaction mixture under reduced pressure and the residue was added with dry ether. The precipitating crystals were filtered out and were dried under reduced pressue to give the titled compound (51 mg, yield 71%).

Melting point: 126°–131° C.
IR spectrum (KBr) cm$^{-1}$: 1700, 1750 (C=O).
NMR spectrum (DMSO-$d_6$) δ ppm: 0.78 (6H, d, J=2 Hz), 2.71 (2H, m), 3.3–3.6 (8H, m), 5.33 (2H, s), 5.7–5.9 (4H, m), 7.43 (10H, s), 8.93 (6H, broad s).

EXAMPLE 5

Meso-2,3-bis(4-acetoxymethyl-3,5-dioxopiperazin-1-yl)butane and
erythro-2-(4-acetoxymethyl-3,5-dioxopiperazin-1-yl)-3-(3,5-dioxopiperazin-1-yl)butane A mixture of meso-2,3-bis(3,5-dioxopiperazin-1-yl)butane (200 mg, 0.7 mmol) and DMF (4 ml) was heated at 110° C. for 10 minutes. To the mixture, 37% aqueous formaldehyde solution (0.2 ml) was added, and then the mixture was stirred at 140° C. for 1.5 hours. The solvent was removed from the reaction mixture under reduced pressure and the residue was added with DMF (4 ml) and pyridine (1 ml) and cooled to −10° C. The cooled mixture was gradually added with acetyl chloride (0.13 ml, 2.0 mmol) and stirred at −10° C. for 1 hour and further at 0° C. for 3 hours. Then, the solvent was removed from the reaction mixture under reduced pressure and the residue was extracted with chloroform. The chloroform solution was washed with diluted hydrochloric acid, aqueous solution of saturated sodium bicarbonate and water, and was dried over anhydrous magnesium sulfate. The solvent was removed from the chloroform solution under reduced pressure and the obtained residue was purified by column chromatography on silica gel, using ethyl acetate-n-hexane (=1:1) as an eluent to give the titled compound.

Meso-2,3-bis(4-acetoxymethyl-3,5-dioxopiperazin-1-yl)butane
  Yield: 92 mg, 32%
  Melting point: 222°–225° C.
Erythro-2-(4-acetoxymethyl-3,5-dioxopiperazin-1-yl)-3-(3,5-dioxopiperazin-1-yl)butane
  Yield: 20 mg, 8%.
  Melting point: 182°–186° C.

EXAMPLE 6

Meso-2,3-bis[4-(3-toluoyloxymethyl)-3,5-dioxopiperazin-1-yl]butane and
erythro-2-[4-(3-toluoyloxymethyl)-3,5-dioxopiperazin-1-yl]-3-(3,5-dioxopiperazin-1-yl)butane A mixture of meso-2,3-bis(3,5-dioxopiperazin-1-yl)butane (200 mg, 0.7 mmol) and DMF (4 ml) was heated at 110° C. for 10 minutes. To the mixture, 37% aqueous formaldehyde solution (0.2 ml) was added, and then the mixture was stirred at 140° C. for 1.5 hours. The solvent was removed from the reaction mixture under reduced pressure and the residue was added with DMF (20 ml) and pyridine (1 ml) and cooled to −10° C. The cooled mixture was gradually added with 3-toluoyl chloride (150 mg, 1.0 mmol) and stirred at −10° C. for 5 hours. Then, the solvent was removed from the reaction mixture under reduced pressure and the residue was extracted with chloroform. The chloroform solution was washed with diluted hydrochloric acid, aqueous solution of saturated sodium bicarbonate and water, and was dried over anhydrous magnesium sulfate. The solvent was removed from the chloroform solution under reduced pressure and the obtained residue was purified by column chromatography on silica gel, using ethyl acetate-n-hexane (=1:1) as an eluant to give the titled compound.

Meso-2,3-bis[4-(3-toluoyloxymethyl)-3,5-dioxopiperazin-1-yl]butane
  Yield: 19 mg, 5%.
  Melting point: 167°–172° C.
Erythro-2-[4-(3-toluoyloxymethyl)-3,5-dioxopiperazin-1-yl]-3-(3,5-dioxopiperazin-1-yl)butane
  Yield: 117 mg, 40%.
  Melting point: 188°–192° C.

CAPABILITY OF EXPLOITATION IN INDUSTRY

As is clear from the foregoing, the compounds (I) of the present invention are novel compounds different in structure from the known bis-dioxopiperazine derivatives, have a broader antitumor spectrum and exhibit by far excellent antitumor activity in comparison with the known antitumor bis-dioxopiperazine (Comparative Compound A). Thus, the compounds of the present invention have wider pharmaceutical usages as antitumor agents.

We claim:

1. A compound represented by the formula (I) or pharmaceutically acceptable salt thereof:

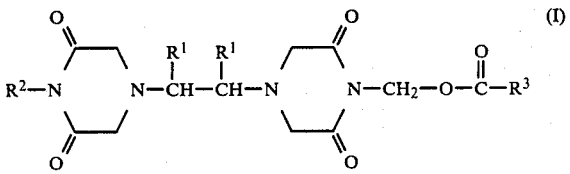

wherein
$R^1$ represents a lower alkyl group;
$R^2$ represents a hydrogen atom or a group of

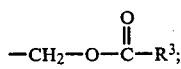

and
$R^3$ represents a lower alkyl group, a phenyl group, a phenyl group substituted with a halogen atom or a lower alkyl group, a furyl group, a styryl group, a styryl group substituted on phenyl nucleus with a halogen atom or a group of —$(CH_2)_n$—$R^4$,

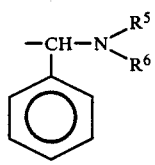

or —$OR^7$ in which
R$^4$ represents a carboxyl group, a phenyl group, a phenyl group substituted with a halogen atom, a phenoxy group or a phenoxy group mono- or di-substituted with a halogen atom,
R$^5$ and R$^6$ respectively represent a hydrogen atom or a protective group for amino group selected from the group consisting of acetyl, tert-butoxycarbonyl and benzyloxycarbonyl,
R$^7$ represents a lower alkyl group, a benzyl group or a benzyl group substituted on phenyl nucleus with a halogen atom or a nitro group, and
n is an integer and 1 or 2.

2. The compound according to claim 1 wherein R$^1$ is methyl, R$^2$ is a group of

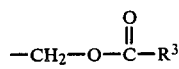

and R$^3$ is an α-aminobenzyl group.

3. The compound according to claim 1 wherein R$^1$ is methyl.

4. The compound according to claim 1 wherein R$^3$ is a lower alkyl group, a phenyl group, a phenyl group substituted with a lower alkyl group, a furyl group, a styryl group, a styryl group substituted on phenyl nucleus with a halogen atom, a benzyl group, a benzyl group substituted on phenyl nucleus with a halogen atom, an α-aminobenzyl group a phenoxymethyl group, a phenoxymethyl group mono- or di-substituted on phenyl nucleus with a halogen atom, a lower alkoxy group, a benzyloxy group or a benzyloxy group substituted on phenyl nucleus with a nitro group.

5. The compound according to claim 1 wherein R$^1$ is methyl and R$^3$ is a lower alkyl group, a phenyl group, a phenyl group substituted with a lower alkyl group, a furyl group, a styryl group, a styryl group substituted on phenyl nucleus with a halogen atom, a benzyl group, a benzyl group substituted on phenyl nucleus with a halogen atom, an α-aminobenzyl group a phenoxymethyl group, a phenoxymethyl group mono- or di-substituted on phenyl nucleus with a halogen atom, a lower alkoxy group, a benzyloxy group or a benzyloxy group substituted on phenyl nucleus with a nitro group.

6. The compound according to claim 1 wherein R$^1$ is methyl and R$^3$ is a lower alkyl group.

7. The compound according to claim 1 wherein R$^1$ is methyl, R$^2$ is a group of

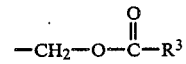

and R$^3$ is methyl.

8. The compound according to claim 1 wherein R$^1$ is methyl and R$^3$ is a phenyl group or a phenyl group substituted with a lower alkyl group.

9. The compound according to claim 1 wherein R$^1$ is methyl and R$^3$ is a phenyl group or a 3-tolyl group.

10. The compound according to claim 1 wherein R$^1$ is methyl, R$^2$ is a hydrogen atom and R$^3$ is a furyl group.

11. The compound according to claim 1 wherein R$^1$ is methyl and R$^3$ is a benzyl group or a benzyl group substituted on phenyl nucleus with a halogen atom.

12. The compound according to claim 1 wherein R$^1$ is methyl and R$^3$ is a 2-chlorobenzyl group.

13. The compound according to claim 1 wherein R$^1$ is methyl and R$^3$ is a phenoxymethyl group or a phenoxymethyl group mono- or di-substituted on phenyl nucleus with a halogen atom.

14. The compound according to claim 1 wherein R$^1$ is methyl, R$^2$ is a hydrogen atom and R$^3$ is a 2,4-dichlorophenoxymethyl group.

15. The compound according to claim 1 wherein R$^1$ is methyl and R$^3$ is a lower alkoxy group.

16. The compound according to claim 1 wherein R$^1$ is methyl and R$^3$ is methoxy or isobutoxy.

17. The compound according to claim 1 wherein R$^1$ is methyl and R$^3$ is a benzyloxy group or a benzyloxy group substituted on phenyl nucleus with a nitro group.

18. The compound according to claim 1 wherein R$^1$ is methyl and R$^3$ is a benzyloxy group or a 4-nitrobenzyloxy group.

19. The compound according to any one of claims 1 to 18, which is a meso- or erythro-form.

20. The compound according to claim 12 wherein the pharmaceutically acceptable salt is trifluoroacetate.

* * * * *